United States Patent
Long et al.

(10) Patent No.: US 11,925,432 B2
(45) Date of Patent: Mar. 12, 2024

(54) SYSTEMS AND METHODS FOR MITIGATING PREMATURE LIGHT DEACTIVATION OF LIGHT DEACTIVATED ADHESIVE DRAPES

(71) Applicant: KCI LICENSING, INC., San Antonio, TX (US)

(72) Inventors: Justin Alexander Long, Wimborne (GB); Timothy Mark Robinson, Blandford Forum (GB); Christopher Brian Locke, Bournemouth (GB)

(73) Assignee: 3M Innovative Properties Company, Saint Paul, MN (US)

( * ) Notice: Subject to any disclaimer, the term of this patent is extended or adjusted under 35 U.S.C. 154(b) by 1043 days.

(21) Appl. No.: 16/644,689

(22) PCT Filed: Sep. 4, 2018

(86) PCT No.: PCT/US2018/049388
§ 371 (c)(1),
(2) Date: Jul. 16, 2020

(87) PCT Pub. No.: WO2019/050855
PCT Pub. Date: Mar. 14, 2019

(65) Prior Publication Data
US 2020/0281678 A1    Sep. 10, 2020

Related U.S. Application Data

(60) Provisional application No. 62/554,280, filed on Sep. 5, 2017.

(51) Int. Cl.
*A61B 46/00* (2016.01)
*A61B 46/20* (2016.01)

(52) U.S. Cl.
CPC .............. *A61B 46/20* (2016.02); *A61B 46/40* (2016.02); *A61B 2046/205* (2016.02)

(58) Field of Classification Search
CPC ... A61B 46/20; A61B 46/40; A61B 2046/205; C09J 7/30; C09J 2301/502;
(Continued)

(56) References Cited

U.S. PATENT DOCUMENTS

2009/0204084 A1* 8/2009 Blott ..................... A61M 3/022
604/290
2009/0216170 A1    8/2009 Robinson et al.

FOREIGN PATENT DOCUMENTS

WO    WO 2014/202935    12/2014

OTHER PUBLICATIONS

International Search Report and Written Opinion issued in corresponding PCT Application No. PCT/US2018/049388, dated Mar. 1, 2019.

* cited by examiner

*Primary Examiner* — Camtu T Nguyen

(57) ABSTRACT

Provided herein is a system and method for mitigating premature light deactivation of light deactivated adhesive drapes. One aspect provides a system comprising a drape, an adhesive layer, and a release agent, where the system is adapted to be coupled to a tissue site and released therefrom upon or after exposure to an external stimulus such as certain wavelengths of light. The system may have a photochromic layer that may transition between a blocking transmittance state and a non-blocking transmittance state to block or allow certain wavelengths of light to pass through. Some systems may use a combination of a photochromic layer and a filter layer to prevent the adhesive from being exposed to deactivation wavelengths prematurely. Another aspect provides a method for application and removal of a drape using (Continued)

by removing one or more of a photochromic layer and a filter layer and applying light to the drape to deactivate the adhesive layer and promote easy, clean, and less painful removal of the drape.

20 Claims, 9 Drawing Sheets

(58) Field of Classification Search
CPC .............. A61F 13/0216; A61F 13/0266; A61F 13/0269; A61F 13/0253; A61F 2013/00289
See application file for complete search history.

SYSTEMS AND METHODS FOR MITIGATING PREMATURE LIGHT DEACTIVATION OF LIGHT DEACTIVATED ADHESIVE DRAPES

CROSS-REFERENCE WITH RELATED APPLICATIONS

This application is a national phase application under 35 U.S.C. § 371 of International Application No. PCT/US2018/049388, filed Sep. 4, 2018, which claims the benefit of the U.S. Provisional Application No. 62/554,280, filed Sep. 5, 2017. The contents of the referenced applications are incorporated herein in their entirety.

BACKGROUND

1. Field of Invention

The present application relates generally to the field of tissue treatment, and more specifically to a system and method for facilitating the application and removal of a drape from a tissue site.

2. Description of Related Art

Systems and devices currently exist for the treatment of tissue, such as wound tissue and skin tissue. Some current tissue treatment systems require the use of an adhesive drape to secure all or a portion of the tissue treatment system to a tissue site. For example, an adhesive drape can be used to secure a gauze portion of a bandage to a wound site by adhering to the skin or other tissue surrounding the wound. Drapes intended for use with negative pressure wound therapy (NPWT) have certain desirable characteristics, not all of which are met by current solutions. Some of these characteristics are that the drape is easy to apply, doesn't adhere well to itself if folded (e.g., adhesive to adhesive) upon application to tissue, achieves a good seal with the tissue, adheres well to tissue and to its film (e.g., polyurethane) covering when layered or overlapped, enables atraumatic removal, is highly breathable, is repositionable upon application, and achieves adhesion that is not affected by patient heat or sweat.

SUMMARY

Certain light sensitive or light deactivated adhesive drape systems have been proposed to allow easier removal of the drape system from a patient. The first generation of these light sensitive or light deactivated adhesive drape systems were sensitive to visible light. These drapes were effective at maintaining a seal until they were exposed to visible light. The visible light would deactivate the adhesive tack of the drape system by crosslinking the adhesive so that it irreversibly transformed the adhesive composition from a viscoelastic state to an elastic state. The obvious limitation to this approach was the need for an opaque cover layer to block out the visible light to prevent premature adhesive cross linking and its subsequent deactivation. Unfortunately, these opaque cover layers meant that these drape systems were not particularly transparent for the clinician or nurse to be able to see the wound or periwound area through the dressing. Another iteration of these light deactivated adhesive drape systems has attempted to address this problem using long wavelength UV light to transform/crosslink the adhesive from a viscoelastic state to an elastic state. However, while an opaque cover layer is not necessary in this type of system to block artificial light, the adhesive drape system is not able to be exposed to sunlight due to the UV light spectra within sunlight. This restricts the ability of the patient to go outside, which can be particularly problematic as patients transition from the acute setting to the post-acute setting where they will be more likely to be exposed to UV sunlight.

To alleviate the existing problems with light deactivated adhesive drape systems, the disclosed embodiments describe a light deactivated adhesive drape system having a photochromic or auto-darkening polymer layer to selectively trigger and further block out/protect the light deactivating adhesive drape system from premature deactivation upon inadvertent exposure to UV light spectra (for example sunlight). The illustrative embodiments described herein are directed to systems and methods for mitigating premature light deactivation of UV light deactivated adhesive drapes.

In some embodiments, a light deactivated adhesive drape system is configured to be coupled to tissue, the system comprising: a drape comprising: a photosensitive adhesive layer having at least one release agent disposed within the adhesive layer, wherein the at least one release agent is configured to weaken a bond of the adhesive layer to the tissue upon exposure to at least one of a plurality of light wavelengths, and a flexible film layer; and a photochromic layer configured to change between a plurality of transmittance states, wherein the plurality of transmittance states includes: a blocking transmittance state configured to block the at least one of the plurality of light wavelengths from passing through the photochromic layer; and a non-blocking transmittance state configured to allow at least some visible light wavelengths to pass through the photochromic layer. In some embodiments, the plurality of light wavelengths include ultraviolet (UV) light wavelengths. In some embodiments, the plurality of light wavelengths are between 280 nm and 385 nm. In some embodiments, the photochromic layer is triggered to change from the non-blocking transmittance state to the blocking transmittance state upon exposure to a plurality of light wavelengths between 375 nm and 385 nm. In some embodiments, the photochromic layer is triggered to change from the blocking transmittance state to the non-blocking transmittance state upon a cessation of exposure to a plurality of light wavelengths between 375 nm and 385 nm. In some embodiments, the photochromic layer comprises glass. In some embodiments, the photochromic layer comprises at least one polymer. In some embodiments, the at least one polymer is one or more of polycarbonate and CR-39. In some embodiments, the glass comprises a plurality of embedded microcrystalline halides. In some embodiments, the plurality of embedded microcrystalline halides comprises silver chloride. In some embodiments, the at least one polymer comprises a plurality of embedded organic photochromic molecules. In some embodiments, the plurality of embedded organic photochromic molecules comprises one or more of oxazines and naphthopyrans. In some embodiments, the photochromic layer is disposed on an outer surface of the drape.

In some embodiments, the system further comprises a filter layer configured to block the at least one of the plurality of light wavelengths that activate the at least one release agent, wherein the plurality of light wavelengths are wavelengths comprising a portion of the visible light spectrum. In some embodiments, the at least one of plurality of light wavelengths is a wavelength in a blue through violet portion of the visible light spectrum. In some embodiments, the filter layer is further configured to allow a plurality of light wavelengths that do not activate the at least one release agent to pass through the filter layer, wherein the plurality of light wavelengths that do not activate the at least one release agent are wavelengths comprising red through green portions of the visible light spectrum. In some embodiments, the filter layer is a printed layer. In some embodiments, the filter layer has one or more of a red and orange color. In some embodiments, the filter layer comprises one or more of a red and orange dye. In some embodiments, the filter layer is disposed between the drape and the photochromic layer. In some embodiments, the filter layer and photochromic layer block some of the same wavelengths. In some embodiments, the some of the same wavelengths include one or more of wavelengths corresponding blue visible light, wavelengths corresponding to violet visible light, and UV wavelengths. In some embodiments, the photochromic layer comprises one or more of a photochromic ink, pigment, and film. In some embodiments, the photochromic layer and the filter layer comprise a single, combined layer. In some embodiments, the photochromic layer is removable from one or more of the drape and the filter layer. In some embodiments, the photochromic layer is configured to be peeled off from an outer surface of one or more of the drape and the filter layer. In some embodiments, the filter layer is removable from the drape. In some embodiments, the filter layer is configured to be peeled off from an outer surface of the drape.

In some embodiments, a light deactivated adhesive drape system is configured to be coupled to tissue, the system comprising: at least one drape comprising: a photosensitive adhesive layer having at least one release agent disposed within the adhesive layer, wherein the at least one release agent is configured to weaken a bond of the adhesive layer to the tissue upon exposure to at least one of a plurality of light wavelengths comprising at least one visible light wavelength and at least one ultraviolet (UV) wavelength, and a breathable layer; a filter layer configured to block the at least one visible light wavelength that activates the at least one release agent; and a photochromic layer configured to change between a plurality of transmittance states, wherein the plurality of transmittance states includes: a blocking transmittance state configured to block the at least one of the plurality of light wavelengths from passing through the photochromic layer; and a non-blocking transmittance state configured to allow the at least one of the plurality of light wavelengths to pass through the photochromic layer. In some embodiments, the photochromic layer comprises one or more of a photochromic ink, pigment, and film. In some embodiments, the photochromic layer and the filter layer comprise a single, combined layer. In some embodiments, the photochromic layer is removable from one or more of the at least one drape and the filter layer. In some embodiments, the photochromic layer is configured to be peeled off from an outer surface of one or more of the at least one drape and the filter layer. In some embodiments, the filter layer is removable from the at least one drape. In some embodiments, the filter layer is configured to be peeled off from an outer surface of the at least one drape. In some embodiments, the at least one visible light wavelength comprises a wavelength in a blue through violet portion of the visible light spectrum. In some embodiments, the at least one UV wavelength is a wavelength between 375 nm and 385 nm.

In some embodiments, a method for using a light deactivated adhesive drape comprises: coupling a light deactivated adhesive drape system to a patient's tissue; removing the photochromic layer from the drape system; exposing the photosensitive adhesive layer to the at least one of the plurality of light wavelengths configured to weaken the bond of the adhesive layer; and removing the drape from the tissue. In some embodiments, removing the photochromic layer from the drape system comprises peeling off the photochromic layer from an outer surface of one or more of the filter layer and the drape. In some embodiments, exposing the adhesive layer to the plurality of light wavelengths comprises exposing the adhesive layer to UV light. In some embodiments, the method further comprises removing the filter layer from the drape system. In some embodiments, removing the filter layer from the drape system comprises peeling off the filter layer from an outer surface of the drape. In some embodiments, exposing the adhesive layer to the plurality of light wavelengths comprises exposing the adhesive layer to wavelengths comprising a portion of the visible light spectrum. In some embodiments, the portion of the visible light spectrum comprises a blue through violet portion of the visible light spectrum.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION

Figure 1A:
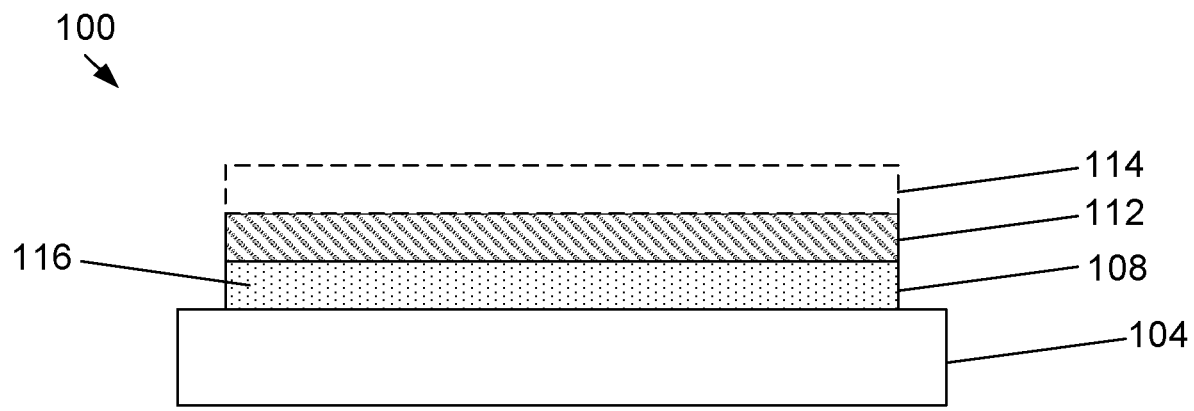
FIGS. 1A-1B are cross-sectional views of a light deactivated adhesive drape system in accordance with an illustrative embodiment of the present disclosure.

In the following detailed description of the preferred embodiments, reference is made to the accompanying drawings that form a part hereof, and in which is shown by way of illustration specific preferred embodiments in which the invention can be practiced. These embodiments are described in sufficient detail to enable those skilled in the art to practice the invention, and it is understood that other embodiments can be utilized and that logical structural, mechanical, electrical, and chemical changes can be made without departing from the spirit or scope of the invention. To avoid detail not necessary to enable those skilled in the art to practice the invention, the description can omit certain information known to those skilled in the art. It is understood that reference to a feature by numeric designation does not necessarily refer only to any particular embodiment depicted in a drawing. The following detailed description is, therefore, not to be taken in a limiting sense, and the scope of the present invention is defined only by the appended claims.

The following definitions are provided to better define the present invention and to guide those of ordinary skill in the art in the practice of the present invention. Unless otherwise noted, terms are to be understood according to conventional usage by those of ordinary skill in the relevant art.

Reduced pressure generally refers to a pressure less than the ambient pressure at a tissue site that is being subjected to treatment. In most cases, this reduced pressure will be less than the atmospheric pressure of the location at which the patient is located. Although the terms "vacuum" and "negative pressure" can be used to describe the pressure applied to the tissue site, the actual pressure applied to the tissue site can be significantly less than the pressure normally associated with a complete vacuum. Consistent with this nomenclature, an increase in reduced pressure or vacuum pressure refers to a relative reduction of absolute pressure, while a decrease in reduced pressure or vacuum pressure refers to a relative increase of absolute pressure.

As used herein, the term "coupled" includes "indirect coupling" via a separate object. For example, a drape can be coupled to the tissue site if both the drape and the tissue site are coupled to one or more third objects, such as a release agent or a second adhesive layer. The term "coupled" also includes "directly coupled," in which case the two objects touch each other in some way. The term "coupled" also encompasses two or more components that are continuous with one another by virtue of each of the components being formed from the same piece of material. Also, the term "coupled" includes chemical coupling, such as via a chemical bond, and electrostatic coupling.

Various aspects of the present invention comprise a system and method for systems and methods for mitigating premature light deactivation of light deactivated adhesive drapes, a portion of which is shown in each of the FIGS. 1A-8. Various embodiments can facilitate the removal of the drape from the tissue site with less trauma to a patient than conventional drapes while preventing premature deactivation of the adhesive. The tissue site may be skin tissue, wound tissue, bone tissue, or any other type of tissue. Various embodiments of the system and method described herein comprise, or can be used with reduced or negative pressure wound healing technology.

Figure 1B:
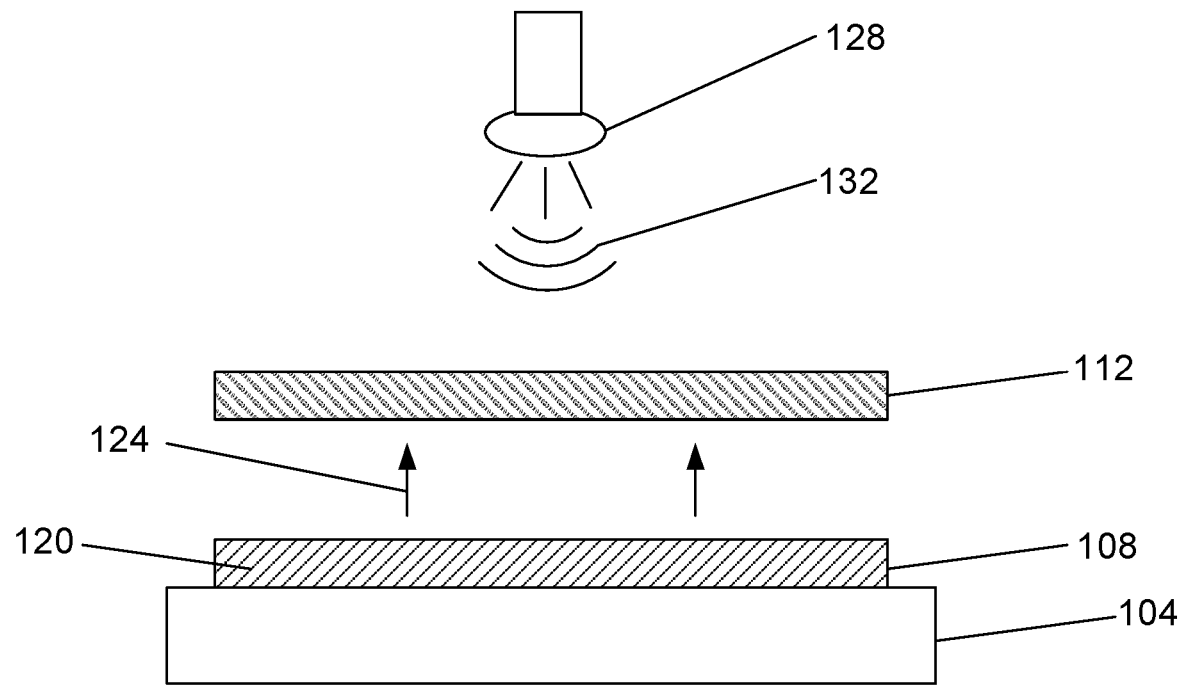

Referring more specifically to FIGS. 1A and 1B, an illustrative embodiment of a light deactivated adhesive drape system 100 disposed onto patient tissue 104 is shown. The system 100 comprises a photosensitive adhesive layer 108 coupled to a flexible film layer 112. In some embodiments, the drape includes both adhesive layer 108 and flexible film layer 112. In the embodiments shown, a drape can be generally understood to be a covering over a tissue 104 that is preferably sterilizable. A drape can comprise a biocompatible thin film material, such as a polymer, a woven or non-woven material, an elastic or non-elastic material, an occlusive or nonocclusive material, and a flexible or inflexible material. A drape can comprise an impermeable, semipermeable, or permeable material. Permeability characteristics can be selected according to desired moisture and gas (e.g., oxygen) transmission. In some embodiments, the drape comprises a material relatively impermeable to moisture and relatively permeable to oxygen. A drape can be coated with a material, for example, to control breathability. A drape can comprise a material which allows or facilitates transmission of external stimuli, such as light, sound, moisture or heat. For example, a drape material can be semi- or substantially transparent to electromagnetic radiation, such as visible, ultraviolet (UV), or infrared light. A drape can be composed of one or more layers. In some embodiments, a drape can be a bilayer drape. For example, a bilayer drape can comprise flexible film layer 112 comprising any biocompatible thin film suitable for tissue or wound contact and a second layer 114 comprising a protective material. As another example, three, four, or more drape layers may be used, with combinations of materials selected according to desired function.

In the embodiment shown, the flexible film layer 112 may be a breathable and/or semiporous film such as polyurethane but other suitable materials may be used. The adhesive layer 108 adheres to the tissue 104 thereby coupling the flexible film layer 112 to the tissue 104. The adhesive layer 108 may cover any portion of the flexible film layer 112 and the tissue 104 as may be required. The adhesive layer 108 can comprise any material, in single or multiple layers, capable of adhering to tissue 104. In some embodiments, prior to the application of a drape to a tissue 104, the adhesive layer 108 can also be covered by an adhesive support layer (not shown). The adhesive support layer can provide rigidity to the drape prior to application and can also aid in the actual application of the drape onto tissue 104. The adhesive support layer can be peeled off or otherwise removed to expose adhesive layer 108 before applying the drape to the tissue. The adhesive layer 108 can comprise one or more materials including, but not limited to, polyurethane, acrylic (e.g., cyanoacrylate), hydrogel, silicon or silicone based material, natural rubber, synthetic rubber, styrene block copolymers, polyvinyl ethers, poly(meth)acrylates, polyolefins, hydrocolloid (e.g., a rubber based hydrocolloid), or a combination thereof. In some embodiments, the adhesive layer 108 comprises a polymer or co-polymer. For example, the adhesive layer 108 can comprise a co-polymer of polyurethane and silicone or various acrylic co-polymers.

The adhesive layer 108 may include at least one release agent 116 comprising a release material. In the embodiment shown, adhesive layer 108 has a plurality of release agents 116 (represented by dots). The release agent 116 can physically or chemically affect adhesion characteristics between a drape and a tissue 104. A release agent 116 can comprise a variety of molecular compositions depending on the particular embodiment being implemented, including but not limited to a photopolymer, an oil particle, a gas particle, a solvent, a lipid, and/or one or more microstructures. Release agents 116 can be present in an inert or inactive form in, on, or near an adhesive layer 108. For example, a release agent 116 can be mixed with the adhesive; on the surface of the adhesive with a random or patterned coverage; coupled to the drape with a random or patterned coverage; or contained within a microstructure located in these or other locations. Upon release or activation, release agents 116 can migrate within the adhesive layer 108 or along an interface between an adhesive layer 108 and a tissue 104 to facilitate the removal of a drape affixed thereto. In the embodiment shown, the release agent 116 is configured to transition from an unreleased state (shown in FIG. 1A) to a release state 120 (represented by diagonal lines in FIG. 1B) to weaken a bond of the adhesive layer 108 to the tissue 104 upon exposure to an external stimulus. Various external stimulus can be employed depending on the particular embodiment being implemented. Non-limiting examples of the external stimulus include electromagnetic (e.g., UV, visible, or infrared light), magnetic, sound, pH, pressure (e.g., positive atmospheric pressure, negative atmospheric pressure, shear force, direct force), thermal, moisture, or a substance. The external stimulus can also be a substance, compound, liquid, or gas capable of reacting with a release agent 116 in adhesive layer 108 such that the release agent 116 transitions from an unreleased state to a released state. In the embodiment shown, the external stimulus is one or more of a plurality of light wavelengths. The weakened bond that occurs as a result of the release of release agent 116 allows a user of the light deactivated adhesive drape system 100 to apply an upward force on flexible film layer 112, such as a force indicated by arrow 124, to remove flexible film layer 112 from tissue 104. The weakened bond reduces the stress applied to tissue 104 in the removal of flexible film layer 112 from tissue 104. Thus, a patient feels less pain and discomfort when the flexible film layer 112 is removed. A residue of molecules from adhesive layer 108 might remain on tissue 104 after removal of flexible film layer 112 depending on a variety of factors such as the type of release agent used.

Referring more specifically to FIG. 1A, in the embodiment shown, release agents 116 are inertly dispersed within adhesive layer 108 and can be located anywhere within adhesive layer 108, as well as any of the outer surfaces of adhesive layer 108, such as an interface between adhesive layer 108 and flexible film layer 112. In some embodiments, release agents 116 can be bonded or coupled directly to flexible film layer 112, and a separate film layer (not shown in FIG. 1A), can separate release agents 116 from adhesive layer 108. In these embodiments, the presence of an external stimulus can weaken, break-down, or increase the permeability of the separate film layer such that release agents 116 are allowed to migrate into adhesive layer 108 to facilitate the removal of flexible film layer 112 from tissue site 105. As shown in FIG. 1B, release agents 116 may be released in the presence of external stimulus such that release agents 116 are allowed to migrate within adhesive layer 108 and the interface between adhesive layer 108 and tissue 104. In the embodiment shown, a UV light source 128 exposes flexible film layer 112 and adhesive 108 to a plurality of light wavelengths 132. In some embodiments, exposure to the plurality of light wavelengths 132 can cause microstructures containing release agents 116 to rupture or tear, thereby releasing release agents 116 from the interior of the microstructures. These released release agents 116 can then be interspersed into adhesive layer 108 and the interface between adhesive layer 108 and tissue 104, thereby weakening the bond between flexible film layer 112 and tissue 104 and facilitating the removal of flexible film layer 112 from tissue 104. As the plurality of light wavelengths 132 reach adhesive 108, release agents 116 may transition from an unreleased state (as shown in FIG. 1A) to a released state 120 (as shown in FIG. 1B) as they are exposed to the plurality of light wavelengths 132. In the embodiment shown, the plurality of light wavelengths 132 are UV wavelengths. In some embodiments, the UV wavelengths may be within a range of 280 nm-380 nm, although it may be preferable to have the UV wavelengths be UVA wavelengths within a range of 315 nm-380 nm.

Referring now to FIGS. 2A-2D, another illustrative embodiment of a light deactivated adhesive drape system 200 disposed onto patient tissue 104 is shown. In this embodiment, light deactivated adhesive drape system 200 is configured to release adhesive layer 108 upon exposure to ambient, visible light instead of UV light. Although having adhesive layer 108 release upon exposure to visible light is advantageous in that it doesn't require a specific UV light source and enables release to occur in any environment having ambient light, it also can increase a likelihood that the adhesive layer 108 will prematurely deactivate. In order to prevent premature deactivation, the adhesive layer 108 may be constructed with release agents 116 that only release upon exposure to certain wavelengths of visible light. For example, in the embodiment shown, release agents 116 will only transition to an unreleased state 120 when exposed to visible light wavelengths in the blue and violet portions of the visible light spectrum. In the embodiment shown, a filter layer 204 is disposed over flexible film layer 112 of the drape. In this embodiment, filter layer 204 is configured to block the visible light wavelengths that release the adhesive layer 108 while allowing other visible light wavelengths to pass through. For example, when exposed to visible light, filter layer 204 will block the blue and violet wavelengths but allow the red, orange, yellow, and/or green wavelengths to pass through. In this way, filter layer 204 is partially transparent and enables a clinician or a nurse to visually inspect the drape and the wound site without premature deactivation of the adhesive layer 108. In some embodiments, filter layer 204 is a colored layer that contains a dye or other coloring agent corresponding to one or more colors of the visible light spectrum that have wavelengths that do not deactivate the adhesive layer 108 (e.g., red, orange, yellow, and/or green). In some embodiments, the filter layer 204 is a film layer or a printed layer disposed over the drape or the adhesive layer 108.

Figure 2A:
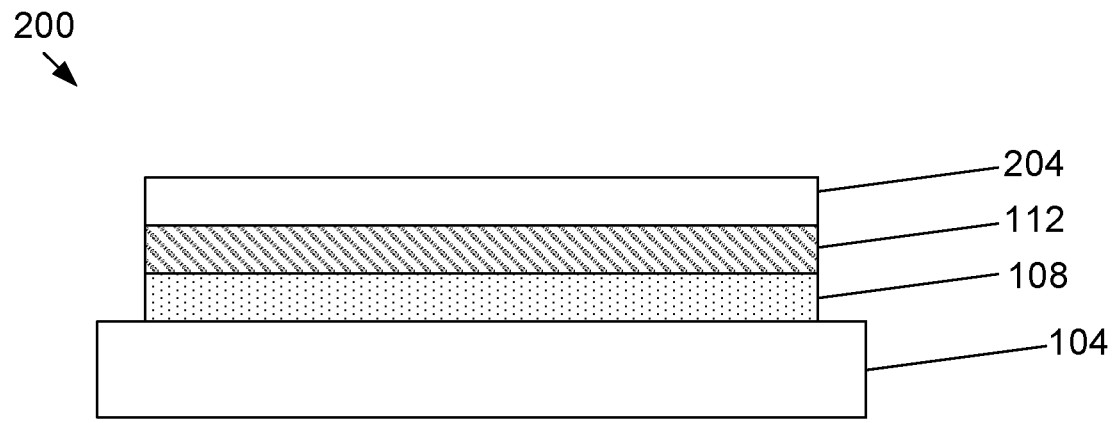
FIGS. 2A-2D are cross-sectional views of a light deactivated adhesive drape system in accordance with another illustrative embodiment of the present disclosure.
Figure 2B:
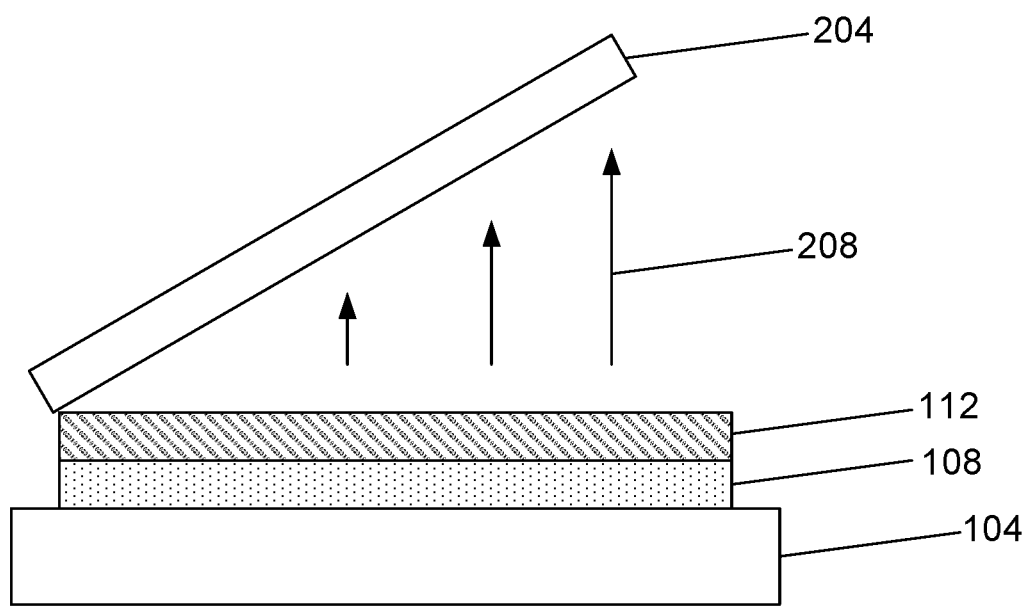
Figure 2C:
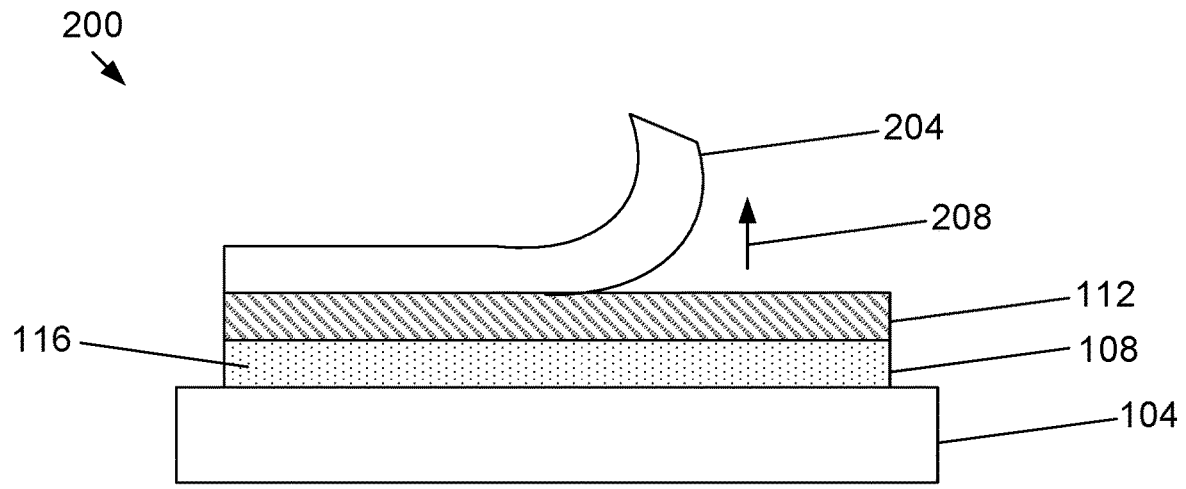
Figure 2D:
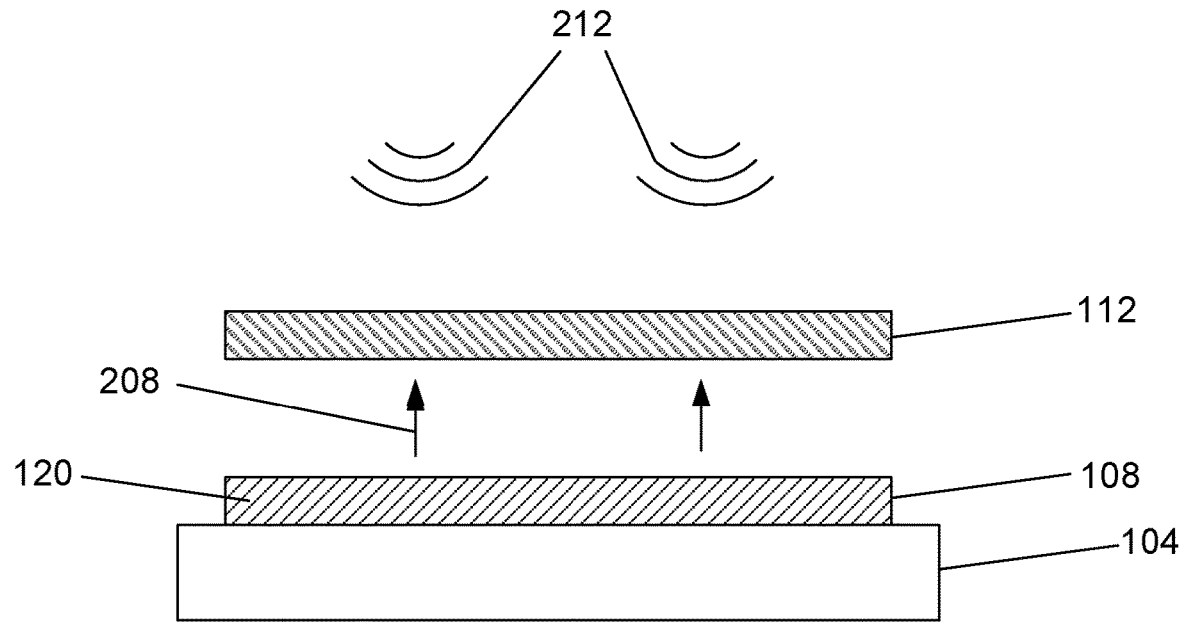

In the embodiment shown in FIG. 2B, filter layer 204 is configured to be removable. This enables the adhesive layer 108 to be deactivated at a time a user desires to remove the drape from tissue 104. In the embodiment shown, filter layer 204 is removed from flexible film layer 112 using an upward or other directional force represented by arrows 208. As shown in FIG. 2C, filter layer 204 can be a film that can be peeled off a surface of flexible film layer 112. However, any suitable method of removing filter layer 204 can be used. Upon removal of the filter layer 204, adhesive layer 108 can be exposed to ambient, visible light 212 that comprises light wavelengths configured to deactivate adhesive layer 108 (e.g., blue and/or violet wavelengths). Upon exposure to ambient light 212, release agents 116 can transition from an unreleased state to a released state 120. The drape including flexible film layer 112 can then be removed from tissue 104. If any residue of adhesive layer 108 remains on tissue 104 after removal of the drape, it may be removed.

Figure 3A:
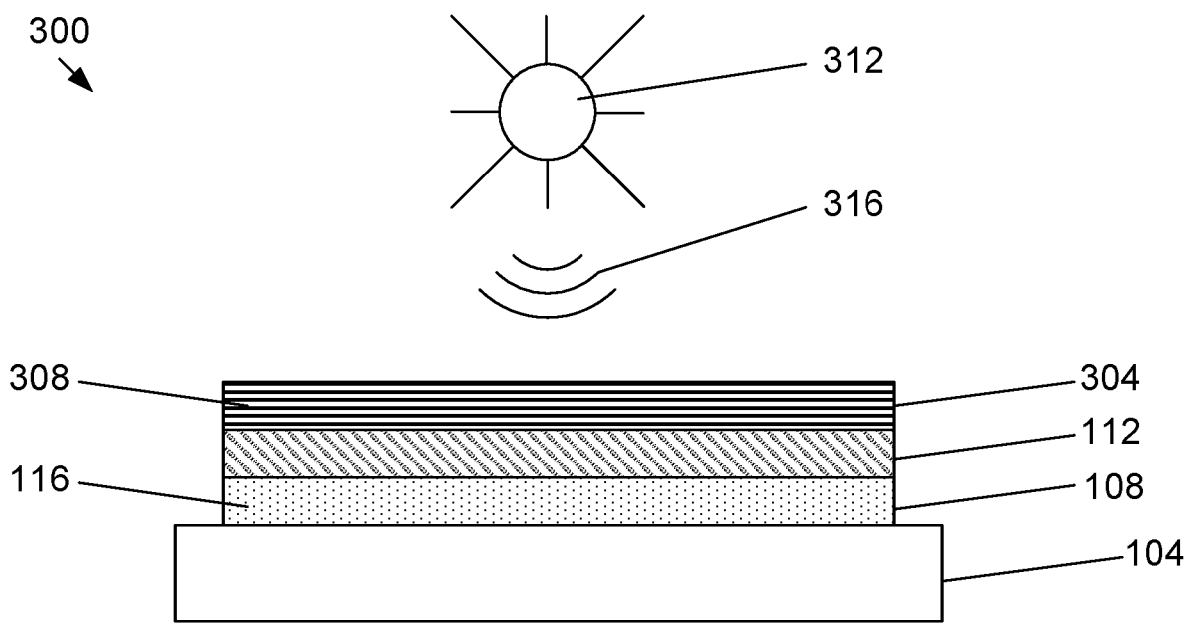
FIGS. 3A-3B are cross-sectional views of a light deactivated adhesive drape system in accordance with another illustrative embodiment of the present disclosure.
Figure 3B:
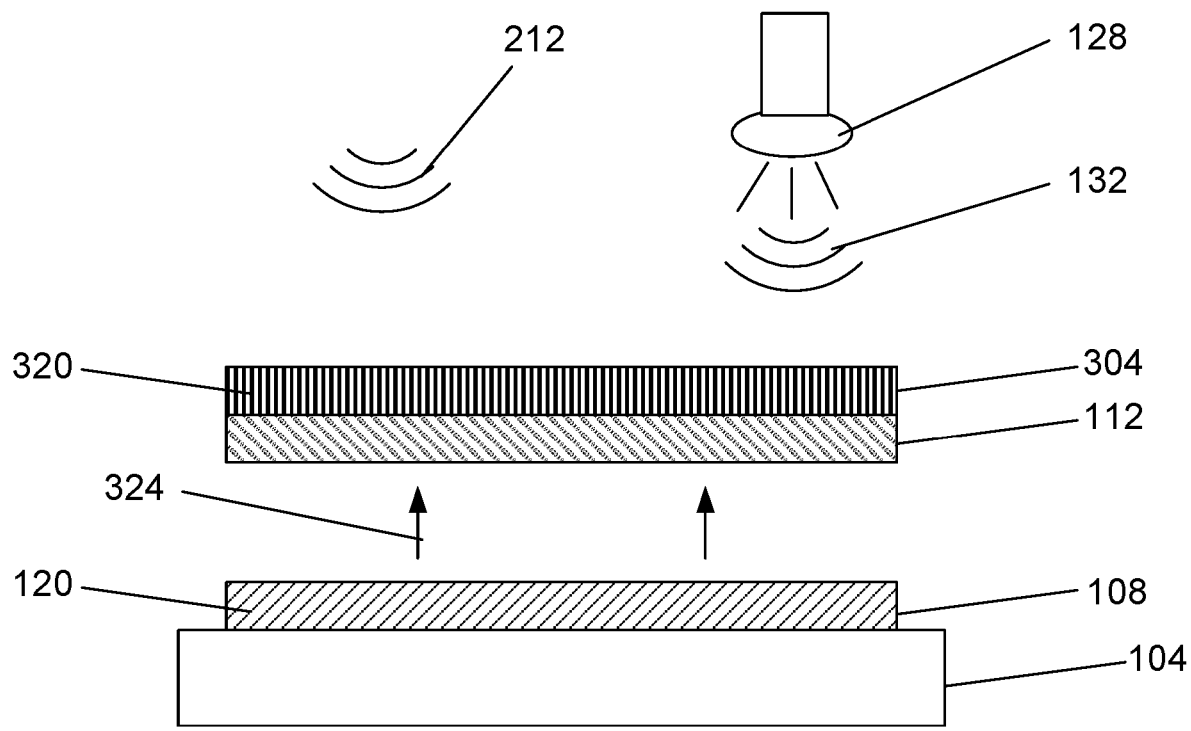

Referring now to FIGS. 3A-3B, another illustrative embodiment of a light deactivated adhesive drape system 300 disposed onto patient tissue 104 is shown. In this embodiment, a photochromic layer 304 is disposed over flexible film layer 112 of the drape. In some embodiments, photochromic layer 304 may be ink, pigment, and/or a film. In some embodiments, photochromic layer 304 is configured to darken upon exposure to specific types of light of sufficient intensity and/or a specific wavelength, most commonly UV radiation. In the absence of activating light, the photochromic layer 304 returns to a clear state. Photochromic layer 304 may be made of glass, plastic, polycarbonate, CR-39, or other polymers. Photochromic layer 304 may darken significantly within seconds of exposure to triggering light wavelengths and take somewhat longer to clear. Photochromic layer 304 may fall within a range of clear and dark transmittances. For example, photochromic layer 304 may have a transmittance reducing from 87% to 20% while another may a transmittance reducing from 45% to 9%. The transmittance and/or material of photochromic layer 304 may be chosen for use with a particular type of deactivating adhesive layer. A glass photochromic layer 304 may achieve photochromic properties through the embedding of microcrystalline silver halides (e.g., silver chloride) within a glass substrate. A plastic photochromic layer 304 may organic photochromic molecules (e.g., oxazines and/or naphthopyrans) to achieve the reversible darkening effect. In these embodiments, organic photochromic molecules can be bathchromically modified to trigger at different wavelengths. A CR-39 photochromic layer 304 may block UV light and therefore be selectively impermeable to UV light spectra but may enable the passage of some visible light for the benefit of the being able to see the underlying drape. Additionally, CR-39 is highly resistant to abrasion. In some of the embodiments shown, photochromic layer 304 may darken when exposed to UV light of the intensity present in sunlight, but not in artificial and/or ambient light. Thus, the use of photochromic layer 304 with light deactivating adhesive drape system 300 make it compatible with indoor and outdoor wear/use.

In the embodiment shown, photochromic layer 304 is configured to change between at least two transmittance states that allow and/or block certain light wavelengths from passing through photochromic layer 304. In a blocking transmittance state 308, photochromic layer 304 blocks certain UV light wavelengths from reaching adhesive layer 108. For example, as shown in FIG. 3A, if the photochromic layer 304 is exposed to the sun 312 and certain light wavelengths 316, photochromic layer 304 will transition to the blocking transmittance state 308 upon reaching a particular triggering wavelength. In some embodiments, the triggering wavelength can be a UV light wavelength. In some embodiments, the triggering wavelength can be in a range of 375 nm-385 nm although other suitable triggering wavelengths can be used. In some embodiments, blocking transmittance state 308 blocks one or more visible light wavelengths from passing through to adhesive layer 108, making the photochromic layer 304 at least partially opaque to the human eye. In the embodiment shown, when photochromic layer 304 is no longer exposed to the triggering wavelength, the photochromic layer 304 may transition to a non-blocking transmittance state 320. In the non-blocking transmittance state 320, photochromic layer 304 allows certain light wavelengths to pass through to the adhesive layer 108. In the embodiment shown, non-blocking transmittance state 320 allows certain ambient light 212 wavelengths to pass through to the adhesive layer 108, making the photochromic layer 304 at least partially transparent to the human eye.

In some embodiments, photochromic layer 304 does not transition based upon exposure to a triggering wavelength but instead transitions upon exposure to a particular light intensity over a certain intensity threshold. For example, in the embodiment shown in FIG. 3A, photochromic layer 304 may transition to blocking transmittance state 308 upon exposure to a high light intensity from sun 312 and may transition back to non-blocking transmittance state 320 when the light intensity falls back below the intensity threshold. Using the embodiment shown in FIG. 3B as an example, photochromic layer has transitioned back to non-blocking transmittance state 320. In this state, a UV light source 128 may apply a plurality of light wavelengths 132 to photochromic layer 304. In the embodiment shown, the intensity of the light emitted by UV light source 128 is not over the light intensity threshold and does not trigger photochromic layer 304 to transition to blocking transmittance state 308. Because photochromic layer 304 is in non-blocking transmittance state 320, it allows the plurality of light wavelengths 132 to reach adhesive layer 108 and deactivate the adhesive. The flexible film layer 112 and photochromic layer 304 can then be removed from tissue 104 with a force represented by arrows 324.

Figure 4A:
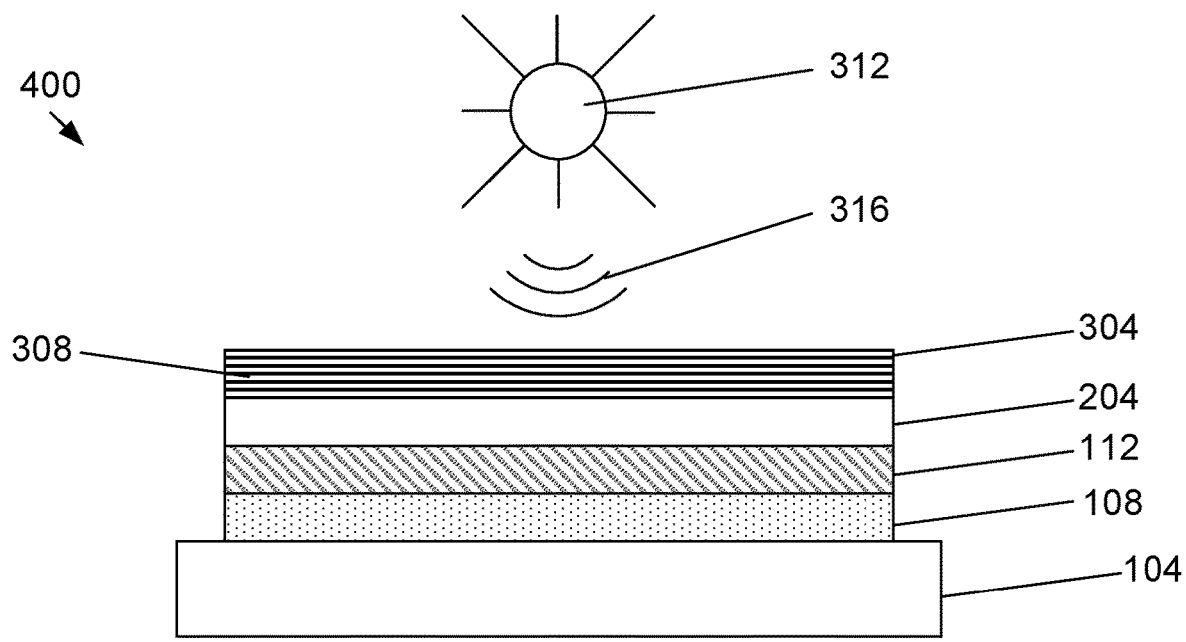
FIGS. 4A-4D are cross-sectional views of a light deactivated adhesive drape system in accordance with another illustrative embodiment of the present disclosure.
Figure 4B:
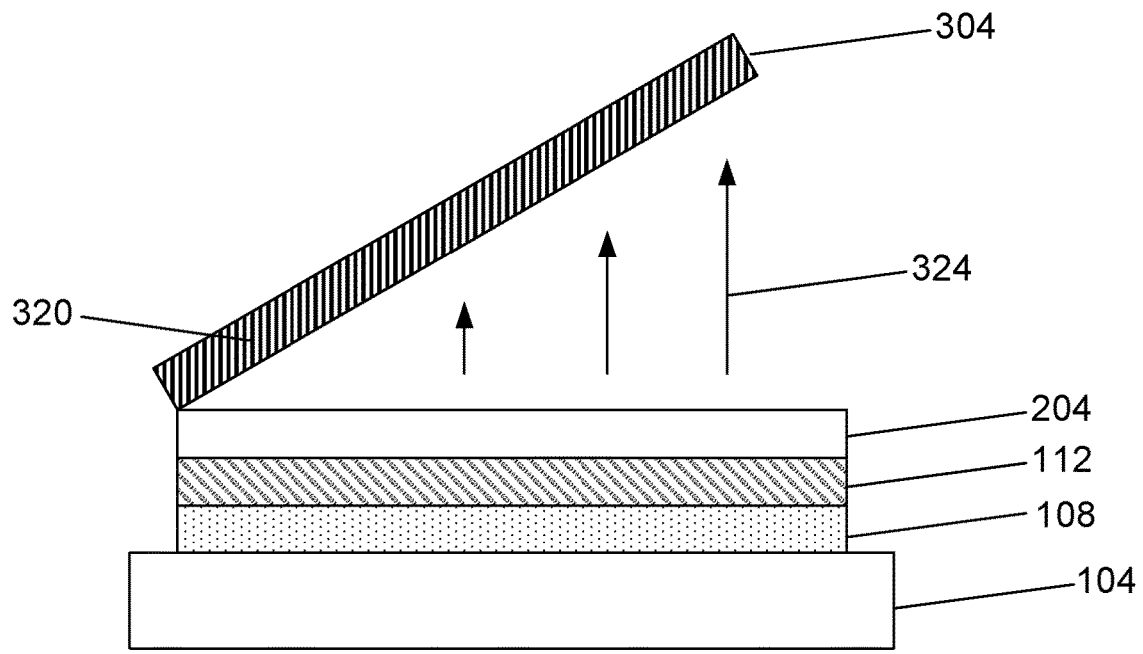

Referring now to FIGS. 4A-4B, another illustrative embodiment of a light deactivated adhesive drape system 400 disposed onto patient tissue 104 is shown. In this embodiment, a photochromic layer 304 is disposed over filter layer 204 which is disposed over flexible film layer 112 of the drape. In some embodiments, photochromic layer 304 can be in same layer as filter layer 204 or on one or more opposite sides of filter layer 204. These embodiments enable the use of an adhesive layer 108 that is deactivated by certain light wavelengths of ambient light 212. In this embodiment, filter layer 204 may be able to filter out the deactivating wavelengths (e.g., blue and violet wavelengths) but may not be able to fully filter the wavelengths at a higher light intensity above a certain intensity threshold. Therefore, photochromic layer 304 can block the deactivating wavelengths by transitioning to blocking transmittance state 308 upon exposure to high light intensity wavelengths or exposure to a triggering wavelength as discussed previously. As shown in FIG. 4A, photochromic layer 304 is exposed to the sun 312 and certain light wavelengths 316 that can deactivate the adhesive layer 108. If the certain light wavelengths 316 are above a certain intensity threshold and/or constitute a triggering wavelength, photochromic layer 304 transitions to blocking transmittance state 308 and blocks all deactivating wavelengths from passing through photochromic layer 304. When photochromic layer 304 ceases to be exposed to certain light wavelengths 316, photochromic layer 304 transitions back to non-blocking transmittance state 320. In the embodiments shown, photochromic layer 304 can be configured to allow certain wavelengths of visible light (e.g., blue and violet wavelengths) that can deactivate the adhesive layer 104 to pass through photochromic layer 304 when in non-blocking transmittance state 320. However, these deactivating wavelengths are filtered out by filter layer 204 while allowing other non-deactivating wavelengths of visible light (e.g., red and orange wavelengths) to pass through to adhesive layer 108. This combination of photochromic layer 304 with filter layer 204 enables a drape configuration that prevents premature deactivation of adhesive layer 108 by blocking all deactivating wavelengths when exposed to both ambient light and UV light, even at high intensities such as sunlight. This combination also enables certain visible light wavelengths of ambient light to pass through the drape to enable a user of the drape to be able to see a condition of a wound in tissue 104 covered by the drape.

Figure 4C:
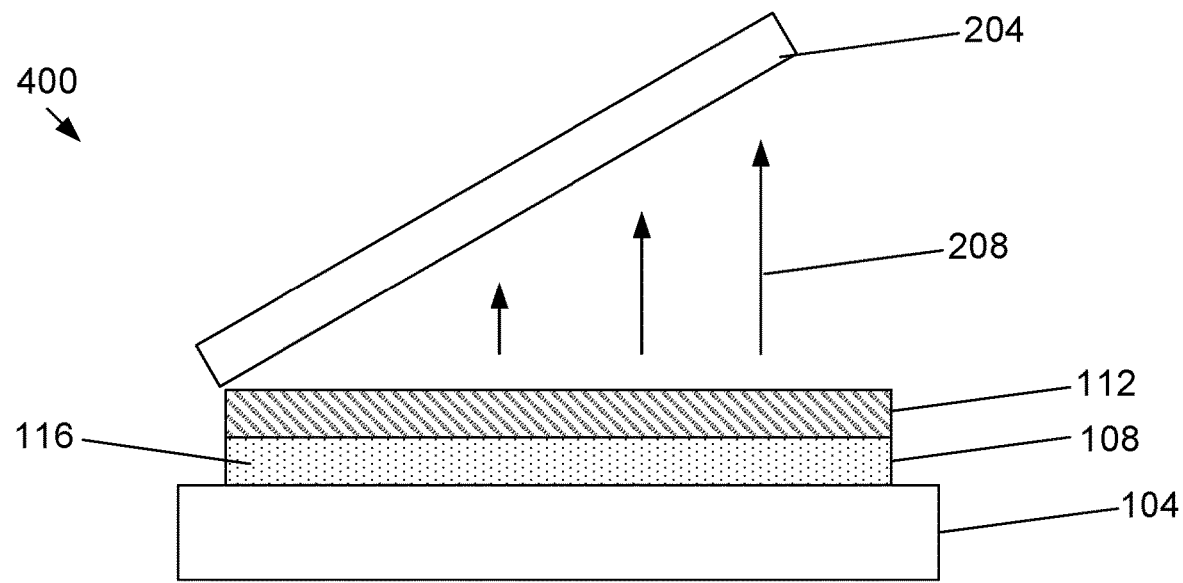
Figure 4D:
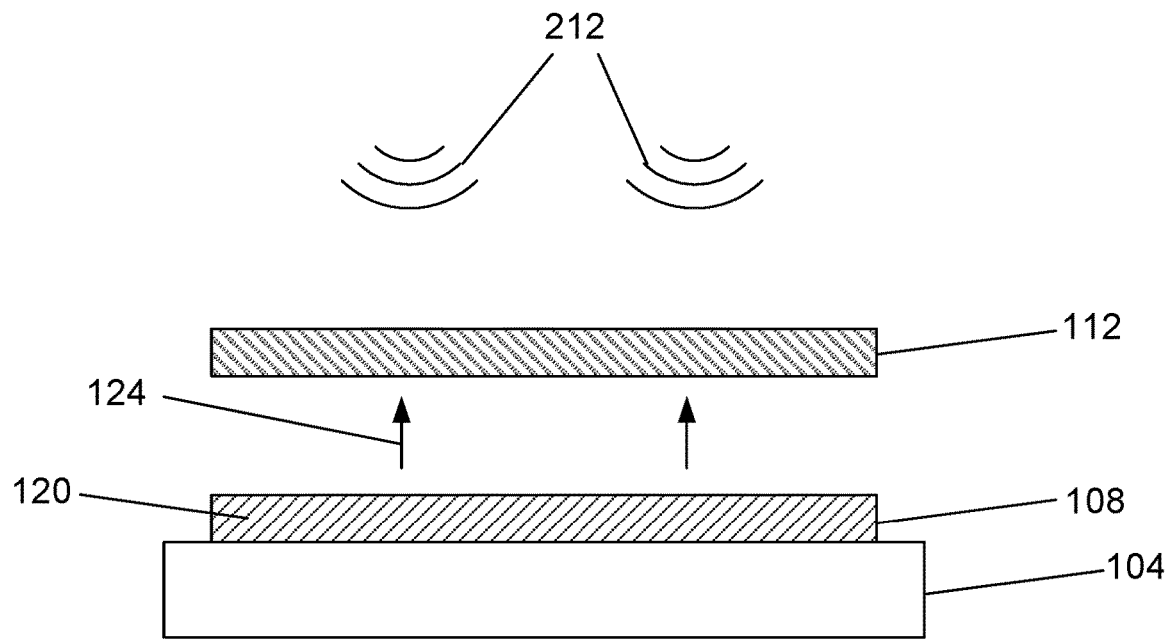

In the embodiment shown in FIG. 4B, photochromic layer 304 is configured to be removable. This enables the adhesive layer 108 to be deactivated at a time a user desires to remove the drape from tissue 104. In the embodiment shown, photochromic layer 304 is removed from flexible film layer 112 using an upward or other directional force represented by arrows 324. Similar to the filter layer 204 shown in FIG. 2C, photochromic layer 304 can be a film that can be peeled off a surface of filter layer 204 or flexible film layer 112. However, any suitable method of removing photochromic layer 304 can be used, including the use of solvents and or other chemical compounds. For example, photochromic layer 304 may be isopropyl alcohol (IPA) or ethanol soluble, which are readily available in hospital setting. This may allow photochromic layer 304 to dissolve upon application of the solvent prior to dressing removal. These embodiments may facilitate easy removal of the photochromic layer 304 with a minimum of residue. As shown in FIG. 4C, upon removal of the photochromic layer 304, filter layer 204 can be removed from flexible film layer 112 using an upward or other directional force represented by arrows 208. As shown in FIG. 4D, upon removal of the photochromic layer 304 and filter layer 204, adhesive layer 108 can be exposed to ambient, visible light 212 that comprises light wavelengths configured to deactivate adhesive layer 108 (e.g., blue and/or violet wavelengths). Upon exposure to ambient light 212, release agents 116 can transition from an unreleased state to a released state 120 and the drape including flexible film layer 112 can be removed from tissue 104.

One disadvantage of using an adhesive that is deactivated by visible, ambient light (where a transparent, removable, and colored filter film 204 is used to remove the activating wavelengths) may occur when multiple, overlapping layers of drapes are applied to a wound. A user would have to remove the filter film 204 from areas of the drape that overlap to enable the activating light to penetrate and reach the adhesive to achieve a full release. This may be difficult and/or time-consuming and may result in patient pain. In some embodiments, an adhesive layer 108 may be used that is deactivated by two types of light wavelengths: one visible and the other UV (i.e., a "pass key" wavelength). In this embodiment, if a user has applied multiple overlapping drape layers and wishes to deactivate the adhesive layer 108 and remove the drape, either removal of the filter layer 204 can be attempted or a 'pass key' wavelength can be applied from an external source. The external source of light could be a torch or flashlight like source 128 emitting, for example, UVA wavelengths, which could pass through the filter layer 204 designed to allow passage of the "pass key" wavelength. In drape embodiments having a photochromic layer 304 in addition to filter layer 204, the "pass key" wavelength can be of a wavelength and/or intensity that does not trigger the photochromic layer 304 to transition to a blocking transmittance state. In this way, the "pass key" wavelength can pass through both the photochromic layer 304 and the filter layer 204 to deactivate the adhesive layer 108 and allow for easy removal of the drape.

Figure 5:
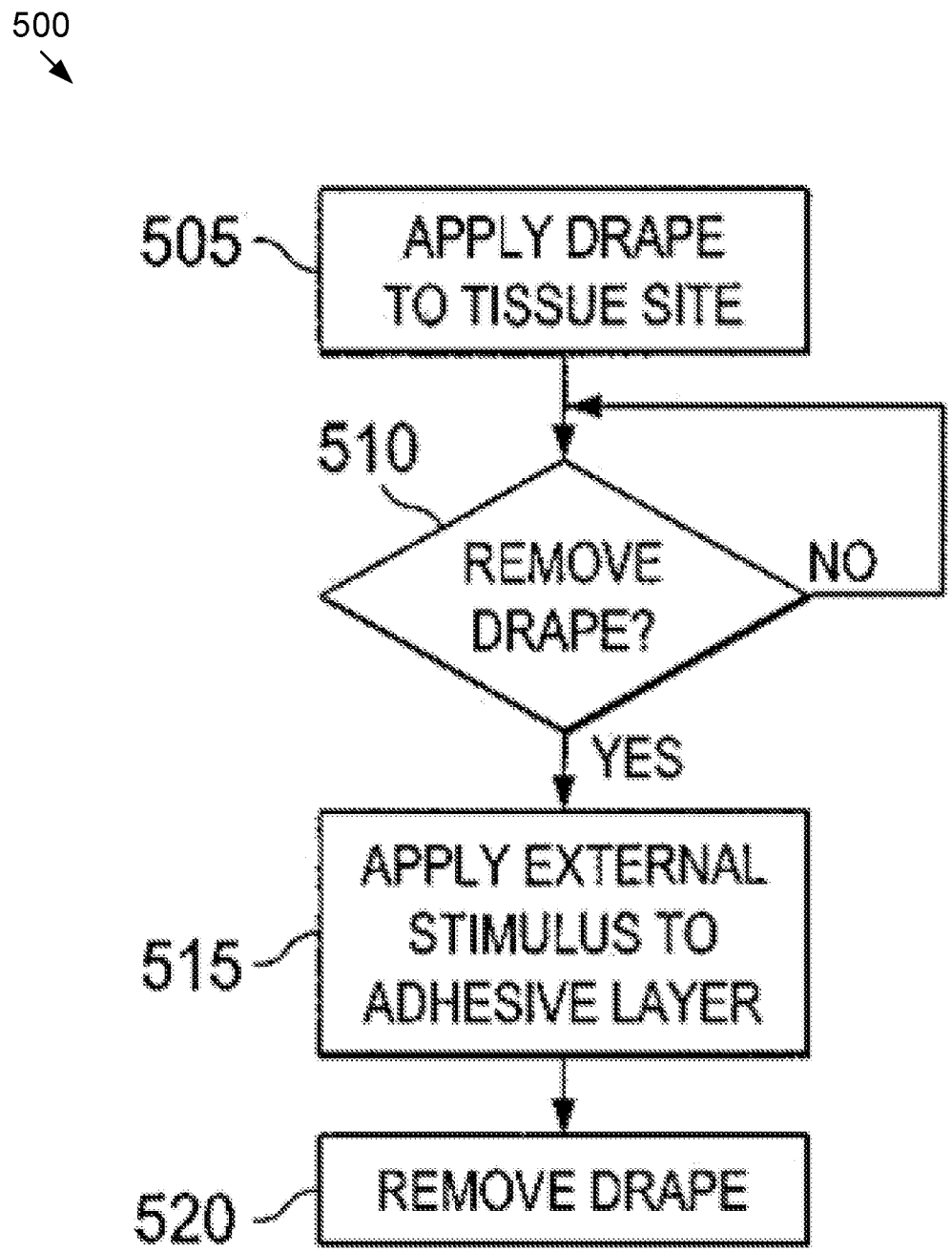
FIG. 5 is a flowchart illustrating a process for using a light deactivated adhesive drape system in accordance with an illustrative embodiment of the present disclosure.

FIG. 5 depicts a flowchart illustrating a general process 500 for facilitating removal of a light deactivated adhesive drape system from a tissue 104 in accordance with an illustrative embodiment of the disclosure. The process illustrated in FIG. 5 can be implemented by a user of a reduced or negative pressure treatment system. The process begins by applying a drape to a tissue 104 (step 505). In this step, adhesive layer 108 can bind to the tissue 104. Also in this step, reduced or negative pressure can be applied to the tissue 104 using a reduced or negative pressure treatment system. The process determines whether to remove the drape from the tissue 104 (step 510). If the process determines not to remove the drape from the tissue 104, the process returns to step 510. If the process determines to remove the drape from the tissue 104, the process applies an external stimulus to the drape, including the adhesive layer 108 coupled to the drape (step 515). In this step, a release agent 116 can be released in accordance with any of the illustrative embodiments described above to facilitate the removal of the drape from the tissue 104. The process then removes the drape from the tissue 104 (step 520).

Figure 6:
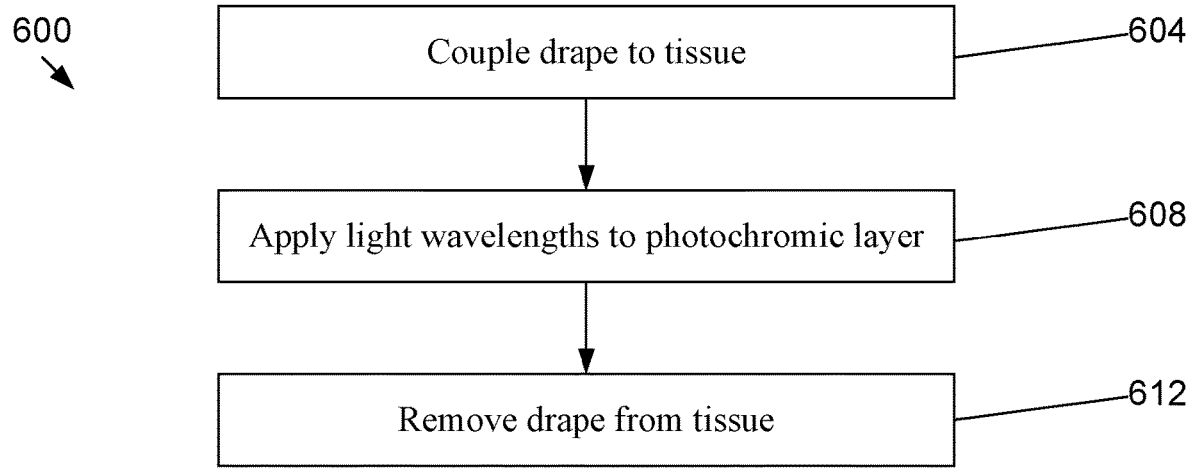
FIG. 6 is a flowchart illustrating a process for using a light deactivated adhesive drape system in accordance with another illustrative embodiment of the present disclosure.
Figure 7:
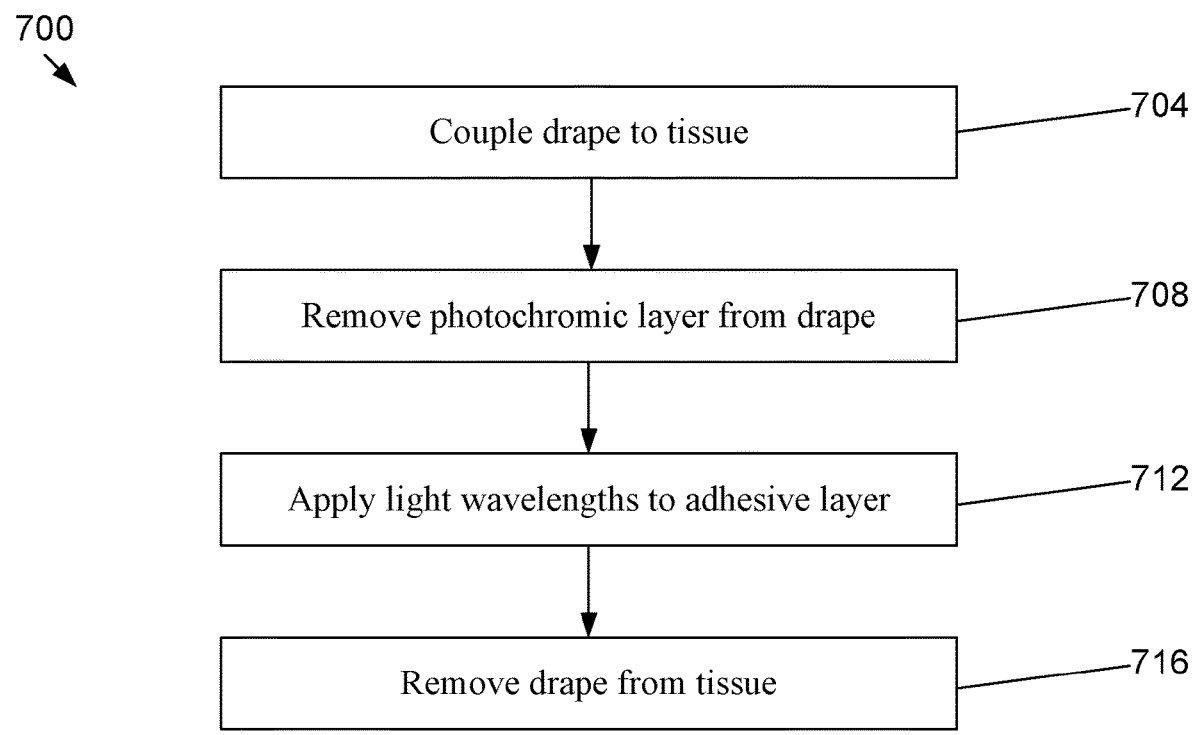
FIG. 7 is a flowchart illustrating a process for using a light deactivated adhesive drape system in accordance with another illustrative embodiment of the present disclosure.
Figure 8:
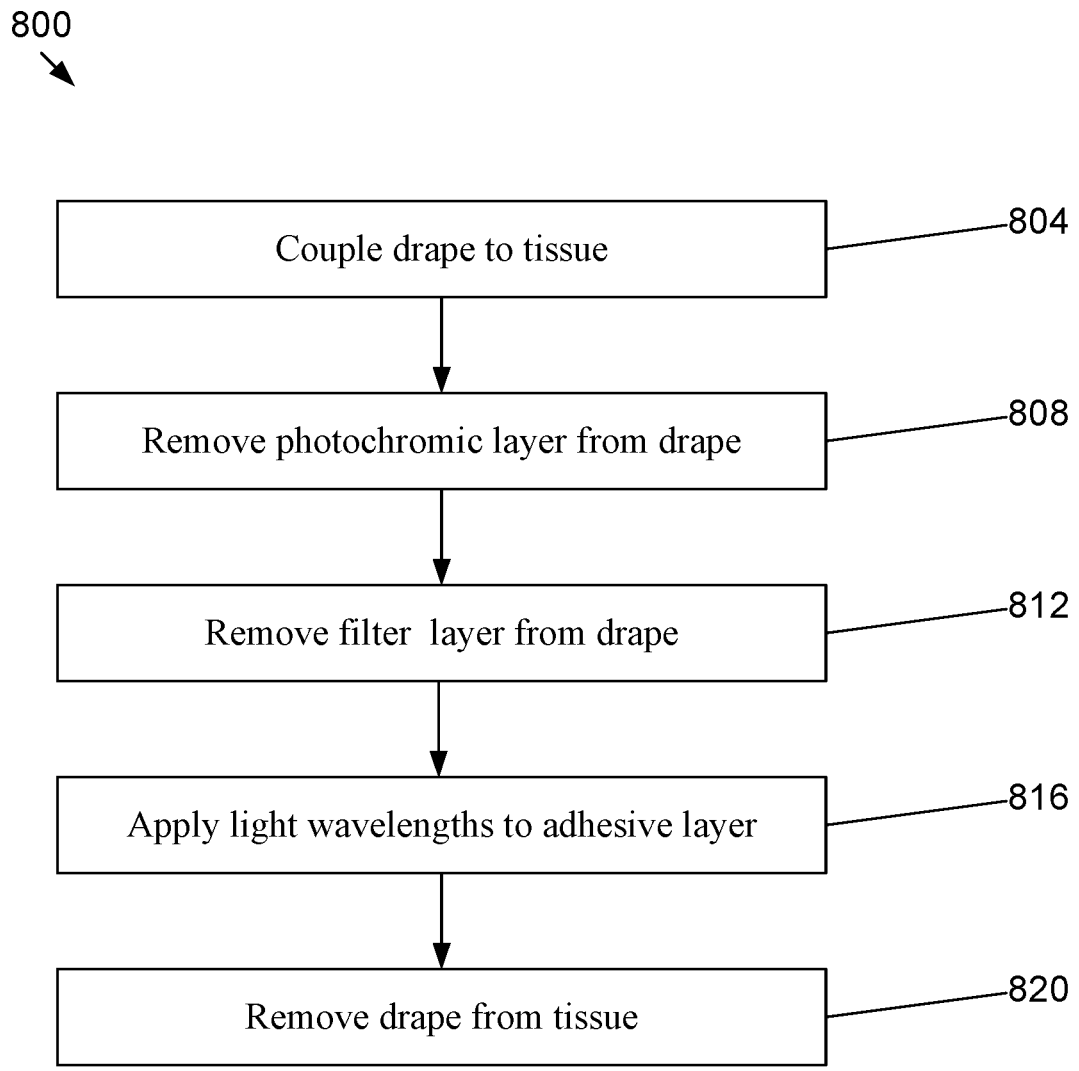
FIG. 8 is a flowchart illustrating a process for using a light deactivated adhesive drape system in accordance with another illustrative embodiment of the present disclosure.

FIGS. 6-8 depict flowcharts illustrating processes 600, 700, 800 for facilitating removal of a light deactivated adhesive drape system from a tissue 104 in accordance with an illustrative embodiment of the disclosure. Referring to FIG. 6, process 600 begins by coupling a drape to a tissue (step 604). In this embodiment, the drape may have a photochromic layer 304 coupled to the embodiments shown in FIGS. 3A-3B. In the embodiments shown, process 600 may be useful with adhesives that are not deactivated by visible light but can be deactivated by exposure to certain wavelengths and/or intensities of UV light. Process 600 continues by, when the drape is desired to be removed, certain deactivating light wavelengths are applied to the photochromic layer (step 608). In this step, the photochromic layer can be in a non-blocking transmittance state to enable the deactivating light wavelengths to pass through the photochromic layer to the adhesive layer and deactivate the adhesive. The process then enables a removal of the drape from the tissue (step 612).

Referring to FIG. 7, process 700 begins by coupling a drape to a tissue 104 (step 704). In this embodiment, the drape may have a photochromic layer 304 coupled to the drape similar to the embodiments shown in FIGS. 3A-3B. In the embodiments shown, process 700 may be useful with photochromic layers that prevent all deactivation wavelengths from reaching the adhesive but may enable some non-deactivating wavelengths to pass through. Process 700 continues by, when the drape is desired to be removed, the photochromic layer is removed from the drape (step 708). Once the photochromic layer is removed from the drape, deactivating light wavelengths are applied to the adhesive layer to deactivate the adhesive (step 712). The process then enables a removal of the drape from the tissue (step 716).

Referring to FIG. 8, process 800 begins by coupling a drape to a tissue 104 (step 804). In this embodiment, the drape may have both a photochromic layer 304 and a filter layer 204 coupled to the drape similar to the embodiments shown in FIGS. 4A-4D. In the embodiments shown, process 800 may be useful with adhesives that are deactivated by certain wavelengths of visible light (e.g., red and orange) and light intensities below a certain intensity threshold but can be deactivated by exposure to certain wavelengths of visible light (e.g., blue and violet) and/or light intensities above the certain intensity threshold. Process 800 continues by, when the drape is desired to be removed, the photochromic layer is removed from the drape (step 808). Once the photochromic layer is removed from the drape, the filter layer is removed from the drape (step 812). Once the filter layer is removed from the drape, deactivating light wavelengths are applied to the adhesive layer to deactivate the adhesive (step 816). The process then enables a removal of the drape from the tissue (step 820).

The flowcharts and block diagrams in the different depicted embodiments illustrate the architecture, functionality, and operation of some possible implementations of the apparatus and methods. In some alternative implementations, the function or functions noted in the block can occur out of the order noted in the figures. For example, in some cases, two blocks shown in succession can be executed substantially concurrently, or the blocks can sometimes be executed in the reverse order, depending upon the functionality involved.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the disclosed methods, devices, and systems are not intended to be limited to the particular forms disclosed. Rather, they include all modifications and alternatives falling within the scope of the claims, and embodiments other than those shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A light deactivated adhesive drape system configured to be coupled to tissue, the system comprising:
    a drape comprising:
        a photosensitive adhesive layer having at least one release agent disposed within the adhesive layer, wherein the at least one release agent is configured to weaken a bond of the adhesive layer to the tissue upon exposure to at least one of a plurality of light wavelengths, and
        a flexible film layer; and
    a photochromic layer configured to darken upon exposure to at least one of a plurality of light wavelengths and change between a plurality of transmittance states, wherein the plurality of transmittance states includes:
    a blocking transmittance state configured to block the at least one of the plurality of light wavelengths from passing through the photochromic layer; and
    a non-blocking transmittance state configured to allow at least some visible light wavelengths to pass through the photochromic layer.

2. The system of claim 1, wherein the plurality of light wavelengths include ultraviolet (UV) light wavelengths.

3. The system of claim 2, wherein the UV light wavelengths are between 280 nm and 385 nm.

4. The system of claim 1, wherein the photochromic layer is triggered to change from the non-blocking transmittance state to the blocking transmittance state upon exposure to a plurality of light wavelengths between 375 nm and 385 nm.

5. The system of claim 1, wherein the photochromic layer is triggered to change from the blocking transmittance state to the non-blocking transmittance state upon a cessation of exposure to a plurality of light wavelengths between 375 nm and 385 nm.

6. The system of claim 1, wherein the photochromic layer comprises glass.

7. The system of claim 6, wherein the glass comprises a plurality of embedded microcrystalline halides, and wherein the plurality of embedded microcrystalline halides comprise silver chloride.

8. The system of claim 1, wherein the photochromic layer comprises at least one polymer.

9. The system of claim 8, wherein the at least one polymer is one or more of polycarbonate or CR-39.

10. The system of claim 9, wherein the at least one polymer comprises a plurality of embedded organic photochromic molecules, and wherein the plurality of embedded organic photochromic molecules comprises one or more of oxazines or naphthopyrans.

11. The system of claim 1, further comprising:
    a filter layer configured to block the at least one of the plurality of light wavelengths that activate the at least one release agent, wherein the plurality of light wavelengths are wavelengths comprising a portion of the visible light spectrum.

12. The system of claim 11, wherein the at least one of plurality of light wavelengths is a wavelength in a blue through violet portion of the visible light spectrum, wherein the filter layer is further configured to allow a plurality of light wavelengths that do not activate the at least one release agent to pass through the filter layer, wherein the plurality of light wavelengths that do not activate the at least one release agent are wavelengths comprising red through green portions of the visible light spectrum.

13. The system of claim 12, wherein the filter layer is a printed layer, wherein the filter is breathable, wherein the filter layer has one or more of a red color or an orange color, and wherein the filter layer comprises one or more of a red dye or an orange dye.

14. The system of claim 11, wherein the filter layer is disposed between the drape and the photochromic layer, and wherein the filter layer and photochromic layer are configured to block some of the same wavelengths.

15. The system of claim 14, wherein the some of the same wavelengths include one or more of wavelengths corresponding blue visible light, wavelengths corresponding to violet visible light, or UV wavelengths.

16. The system of claim 11, wherein the photochromic layer comprises one or more of a photochromic ink, a pigment, or a film.

17. The system of claim 11, wherein the photochromic layer and the filter layer comprise a single, combined layer.

18. The system of claim 11, wherein the photochromic layer is removable from one or more of the drape or the filter layer, and wherein the photochromic layer is configured to be peeled off from an outer surface of one or more of the drape or the filter layer.

19. A method comprising:
    coupling a light deactivated adhesive drape system to a patient's tissue, wherein the light deactivated adhesive drape system includes:
        a drape comprising:
            a photosensitive adhesive layer having at least one release agent disposed within the adhesive layer, wherein the at least one release agent is configured to weaken a bond of the adhesive layer to the tissue upon exposure to at least one of a plurality of light wavelengths, and
            a flexible film layer; and
        a photochromic layer configured to darken upon exposure to at least one of a plurality of light wavelengths and change between a plurality of transmittance states, wherein the plurality of transmittance states includes:
            a blocking transmittance state configured to block the at least one of the plurality of light wavelengths from passing through the photochromic layer: and
            a non-blocking transmittance state configured to allow at least some visible light wavelengths to pass through the photochromic layer:
    removing the photochromic layer from the drape system;
    exposing the photosensitive adhesive layer to the at least one of the plurality of light wavelengths configured to weaken the bond of the adhesive layer; and
    removing the drape from the tissue.

20. The method of claim 19, wherein removing the photochromic layer from the drape system comprises peeling off the photochromic layer from an outer surface of one or more of the filter layer or the drape.

\* \* \* \* \*